United States Patent
Zhang et al.

(10) Patent No.: US 10,227,483 B2
(45) Date of Patent: Mar. 12, 2019

(54) COMPOSITIONS OF OLEFIN BLOCK COPOLYMERS AND PROPYLENE-BASED ELASTOMERS

(71) Applicant: ExxonMobil Chemical Patents Inc., Baytown, TX (US)

(72) Inventors: Jingwen Zhang, Houston, TX (US); Carlos R. Lopez-Barron, Houston, TX (US); Jan Kalfus, Spring, TX (US); Abdul M. Jangda, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/626,581

(22) Filed: Jun. 19, 2017

(65) Prior Publication Data

US 2018/0079900 A1 Mar. 22, 2018

Related U.S. Application Data

(60) Provisional application No. 62/397,378, filed on Sep. 21, 2016.

(51) Int. Cl.
| | | |
|---|---|---|
| *C08L 23/14* | (2006.01) | |
| *C08L 53/00* | (2006.01) | |
| *A61L 15/22* | (2006.01) | |

(52) U.S. Cl.
CPC .............. *C08L 23/14* (2013.01); *A61L 15/225* (2013.01); *C08L 53/005* (2013.01); *C08L 2203/02* (2013.01)

(58) Field of Classification Search
CPC ................................ C08L 23/14; C08L 53/005
See application file for complete search history.

(56) References Cited

U.S. PATENT DOCUMENTS

| | | | |
|---|---|---|---|
| 7,067,591 B2 | 6/2006 | Abe | |
| 7,807,241 B2 | 10/2010 | Sasagawa et al. | |
| 7,858,706 B2 | 12/2010 | Arriola et al. | |
| 8,052,822 B2 | 11/2011 | Datta et al. | |
| 8,071,681 B2 | 12/2011 | Iyer et al. | |
| 2002/0156185 A1* | 10/2002 | Adedeji | B29B 7/421 525/88 |
| 2009/0023826 A1 | 1/2009 | Nishimura et al. | |
| 2009/0246518 A1* | 10/2009 | Fujimura | B32B 27/36 428/339 |
| 2011/0319548 A1* | 12/2011 | Hoya | C08L 23/14 524/505 |
| 2013/0209763 A1* | 8/2013 | Maeda | D04H 1/559 428/212 |
| 2015/0010765 A1 | 1/2015 | Munro et al. | |
| 2018/0002485 A1* | 1/2018 | Tanigawa | C08G 73/10 |

FOREIGN PATENT DOCUMENTS

| | | |
|---|---|---|
| WO | 2006/101924 A | 9/2006 |
| WO | 2006/102154 A | 9/2006 |

OTHER PUBLICATIONS

Agilent molecular weight pdf (Year: 2015).*
Sakurai et al., "Blends of Amorphous-crystalline Block Copolymers With Amorphous Homopolymers. Morphological Studies by Electron Microscopy and Small Angle Scattering," Polymer, vol. 37, No. 20, pp. 4443-4453, 1996.

* cited by examiner

*Primary Examiner* — Mark S Kaucher
(74) *Attorney, Agent, or Firm* — Kevin M. Faulkner

(57) ABSTRACT

Polymer blends comprising at least one olefin block copolymer such as poly(ethylene-b-ethylene/propylene-b-ethylene), and at least one propylene-based elastomer such as a propylene-ethylene random copolymer, such blends useful in elastic hygiene articles. The blends have improved permanent set compared to the propylene-based elastomer alone.

38 Claims, 6 Drawing Sheets

COMPOSITIONS OF OLEFIN BLOCK COPOLYMERS AND PROPYLENE-BASED ELASTOMERS

PRIORITY CLAIM

This application claims priority to and the benefit of U.S. Ser. No. 62/397,378, filed Sep. 21, 2016 and is incorporated by reference in its entirety.

FIELD OF THE INVENTION

The present invention relates to olefin block copolymer blends with an elastomer, and more particularly to blends of olefin block copolymers with propylene-based elastomers suitable for elastic hygiene articles.

BACKGROUND

The elastic hygiene market is a large and fast growing market. Elastic polymers that are able to keep their shape upon deformation (low permanent set) are highly desirable in elastic hygiene articles such as diapers. Styrenic block copolymers (SBC's) have long been the workhorse in this market due to their excellent elastomeric properties at body temperature. There have been attempts to approach the elastic behavior of SBCs in newer polyolefins. Commercial block copolymers (OBC's) such as Infuse™ olefin block copolymers sold by The Dow Chemical Company, and copolymers such as Vistamaxx™ propylene-based elastomers (PBEs) sold by ExxonMobil Chemical Company, are less expensive to manufacture than SBC's but show lower elastomeric performance at body temperature than typical SBC's due to the differences in their molecular architectures. Alone, such OBC's and PBE's have largely been inadequate in elastic hygiene applications.

Synthesized via living anionic polymerization, manufacturers of SBCs can have precise control over the number of blocks and the block lengths with a nearly uniform distribution of molecular weights. The glassy block contains a high ratio of polystyrene and the rubbery block contains a high ratio of polyisoprene, polybutadiene or their hydrogenated versions: poly(ethylene-alt-propylene) or poly(ethylene-alt-butene). This is highly desirable. One problem with such SBCs is their expense. It would be desirable to have compositions that are elastic and deformable like SBCs but at a lower cost.

Relevant publications include U.S. Pat. No. 8,071,681; U.S. Pat. No. 8,052,822; U.S. Pat. No. 7,858,706; U.S. Pat. No. 6,635,715; EP 1 858 942 A1; EP 1 871 816 A1; EP 1 882 715 A1; EP 1 623 822 A1; EP 2 832 171; and WO 2002/066540; and K. Sakurai et al. "Blends of amorphous-crystalline block copolymers with amorphous homopolymers. Morphological Studies by electron microscopy and small angle scattering," in 37(20) POLYMER 4443 (1996).

SUMMARY

Disclosed herein is a polymer blend comprising (or consisting essentially of, or consisting of) at least one olefin block copolymer ("OBC"), preferably poly(ethylene-b-ethylene/propylene-b-ethylene); and at least one propylene-based elastomer.

Also disclosed is a polymer blend comprising within a range from 5, or 10, or 15 wt % to 30, or 40, or 50 or 60 wt % of the OBC, and within a range from 40, or 50, or 60, or 70 wt % to 85, or 90, or 95 wt % of the propylene-based elastomer.

Also disclosed is an OBC comprising an ethylene/propylene block having a propylene content within a range from 50 wt % to 70 wt % by weight of the ethylene/propylene block.

Also disclosed is an OBC comprising an ethylene block having a C3 to C8 content within a range from 2 wt % to 6, or 8, or 10, or 15 wt % by weight within each ethylene block.

DETAILED DESCRIPTION

Figure 1:
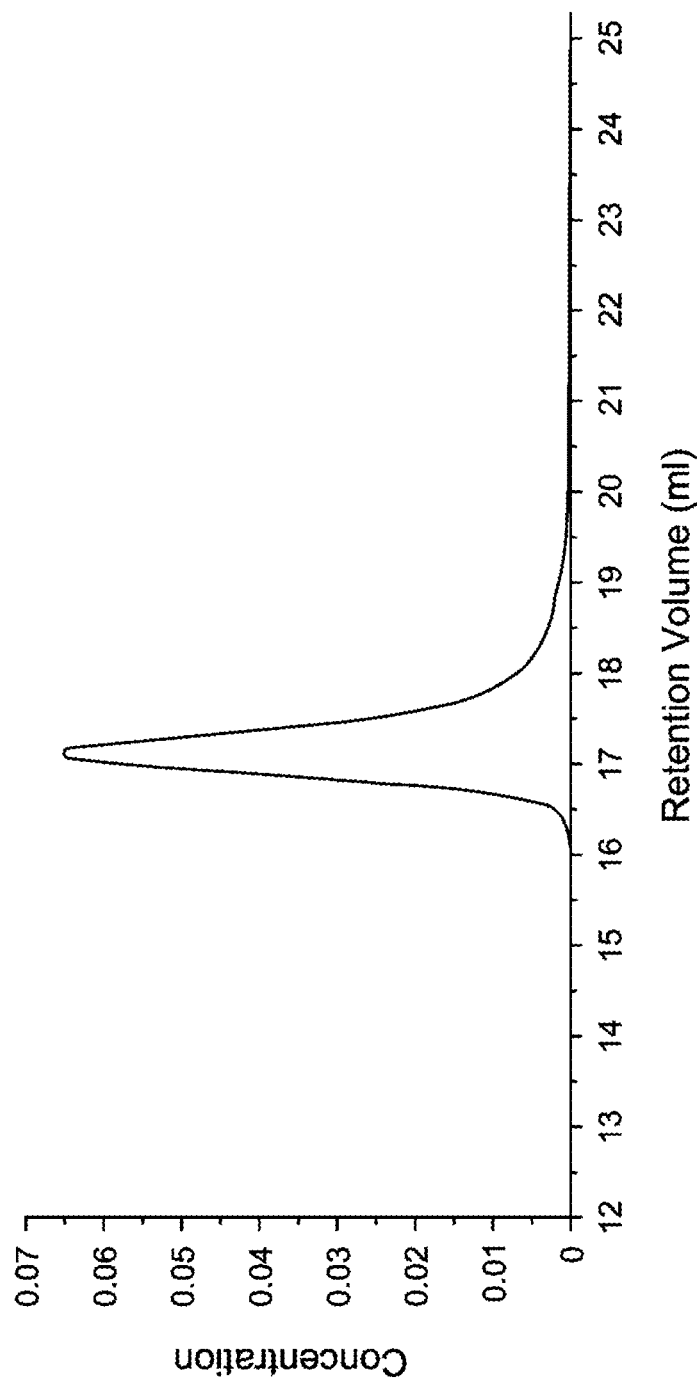
FIG. 1 is a gel permeation chromatographic (GPC) trace of the neat EEP$_r$E of the examples.

The problems described above are addressed by this disclosure of a composition comprising (or consisting essentially of, or consisting of) at least one OBC; and at least one propylene-based elastomer. In any embodiment, the OBC is poly(ethylene-b-ethylene/propylene-b-ethylene). In any embodiment, the poly(ethylene-b-ethylene/propylene-b-ethylene) is derived from hydrogenated poly(1,4-butadiene-b-isoprene-b-1,4-butadiene) preferably made in a living anionic polymerization process. In any embodiment, the composition comprises within a range from 5, or 10, or 15 wt % to 30, or 40, or 50, or 60 wt % of the OBC, and within a range from 40, or 50, or 60, or 70 wt % to 85, or 90, or 95 wt % of the propylene-based elastomer. The compositions disclosed herein are useful in elastic hygienic articles such as infant and adult diapers, disposable cloths, surgical wear, other hygiene wear and undergarments, and other absorbent wear.

Aspects of the inventive compositions are described here.

Olefin Block Copolymer

The OBCs of the present invention(s) preferably comprise alternating blocks of a crystalline polyolefin "A" and an amorphous polyolefin "B." The OBCs are formed by first synthesizing a pre-polymer, typically by living anionic polymerization, followed by hydrogenation of the product. Most preferably, the OBCs comprise one or more crystalline-amorphous units, wherein each crystalline-amorphous unit is composed of a single crystalline "A" block and a single amorphous "B" block. Such a structure can be represented by the following formula:

wherein n is an integer of at least 1, preferably greater than 0.5, or 1, or 2, or 4, or 10, or 20; or within a range from 1, or 2, or 4, to 10, or 20. Preferably n is within a range from 0.5 to 3 or 4. Most preferably, n is 1 for triblock or 0.5 for diblock.

Anionic polymerization of multi-olefin monomers such as isoprene and butadiene is well known in the art. For instance, in any embodiment, the anionic polymerization is lithium-ion initiated. Suitable lithium-ion initiators include, but are not limited to, organolithium compounds, more preferably a compound formed from diisopropenylbenzene and a tertiary alkyl lithium compound, for example, m-di-(1-methyl-3,3-dimethylbutyllithio)benzene.

Depending upon the reactivity of the reagents used and the polymerization conditions, the anionic polymerization process can be run at temperatures varying from 0° C. to 200° C. as limited by thermal stability of the monomer, the lithium initiator, and the polyolefin "A" and/or "B" pre-polymer products. Temperatures between 0° C. and 150° C. are preferred, more preferably from 30° C. to 100° C., most preferably from 40° C. to 60° C. Polymerization times may range between several seconds and a few days, more preferably ranging from one to ten hours.

A wide range of solvents and/or solvent blends may be used as the medium in which the anionic polymerization is run. Solvents that are particularly suited for solvating the lithium initiator include, but are not limited to cyclohexane, tetrahydrofuran (THF) and diethyl ether. A high polarity solvent is preferred for synthesizing polybutadiene with a vinyl content, that is, 1,2-addition content, of preferably greater than 25 mol %, and most preferably greater than 35 mol %.

Preferably, the OBC comprising the polyolefin "A" and polyolefin "B" pre-polymer could by synthesized via hydrogenating from blocks of "A" and "B" that contains double bonds. Such hydrogenation may be carried out by any conventional methods known in the art. For purposes of the present disclosure, "substantially saturated" as it refers to the OBC means that the copolymer includes on average fewer than 5 double bonds, or fewer than 3 double bonds, or fewer than 1 double bond, or fewer than 0.5 double bond per one hundred carbon in the copolymer chain.

Hydrogenation can be carried out in the process of the present disclosure by any known catalysis system, including heterogeneous systems and soluble systems. Preferably, a transition metal based catalyst, more preferably a ruthenium or rhodium based catalyst, most preferably Wilkinson's catalyst (chlorotris(triphenylphosphine) rhodium(I)), is used to catalyze the hydrogenation.

Alternatively, the hydrogenation may be performed in the absence of a catalyst. Non-catalyzed hydrogenation is preferably performed using an inorganic reducing agent, preferably a diimide. Preferably, the diimide is generated through thermal treatment of an arenesulfonylhydrazide, most preferably p-toluenesulfonulhydrazide.

The hydrogenation reaction herein can be accomplished at a temperature high enough to prevent hydrogenated polyolefins from crystallizing in solution, preferably at a temperature ranging from 40° C. to 160° C. and most preferably from 60° C. to 150° C. Different substrates being hydrogenated will require different optimum temperatures, which can be determined by experimentation. The initial hydrogenation pressures may range up to 3,000 psi partial pressure, at least part of which is present due to the hydrogen. Pressures from 1 to 7500 psig are suitable. Preferred pressures are up to 2000 psig, and most preferred pressures are from 100 to 1000 psig are employed. The reactive conditions are determined by the particular choices of reactants and catalysts. The process may be either batch or continuous. In a batch process, reaction times may vary widely, such as between 0.01 seconds to 10 hours. In a continuous process, reaction times may vary from 0.1 seconds to 120 minutes and preferably from 0.1 seconds to 10 minutes.

In any embodiment, the polyolefin "A" of the OBC pre-polymer is synthesized via the anionic polymerization of butadiene. Once hydrogenated, the "A" block is a crystalline block comprising ethylene and less than 5, or 4, or 3, or 2, or 1 wt % C3 to C8 α-olefin derived units by weight of the "A" block. More particularly, the "A" blocks comprise greater than 85 or 95 wt % ethylene and are thus called "ethylene blocks," wherein each ethylene block of the A-B-A OBC, poly(ethylene-b-ethylene/propylene-b-ethylene), has a C3 to C8 content within a range from 1, or 2, or 3 wt % to 5, or 6, or 8, or 10, or 15 wt % by weight within each ethylene block. More preferably, in any embodiment the ethylene blocks consist of ethylene-derived units and C3 to C8-derived units, most preferably ethylene- and 1-butene-derived units.

Preferably, the crystalline polyolefin "A" block(s) of the OBC comprise ethylene derived monomer units. Preferably, each polyolefin "A" block has an ethylene content of greater than 90 mol % based on the total moles of the monomers of polyolefin "A." More preferably, each polyolefin "A" block has an ethylene content of greater than 95, or 98, or 99 mol %. Most preferably, each polyolefin "A" block has an ethylene content of greater than 99.9 mol %. Preferably, each polyolefin "A" block has a degree of crystallinity greater than 50%, more preferably greater than 60%, and most preferably greater than 70%.

In any embodiment, the polyolefin "B" component of the pre-polymer is synthesized via the anionic polymerization of isoprene monomer. Once hydrogenated, the "B" block is a non-crystalline or elastomeric α-olefin copolymer comprising alternating ethylene- and propylene-derived units with 50 mol % propylene-derived units. In any embodiment, the "B" block is an ethylene/propylene block of the poly(ethylene-b-ethylene/propylene-b-ethylene) has a propylene content within a range from 50 wt % to 70 wt % by weight of the ethylene/propylene block; wherein the ethylene/propylene block consists of ethylene-derived units and propylene-derived units.

The A-B-A OBC described herein is preferably a poly (ethylene-b-ethylene/propylene-b-ethylene) block copolymer ("EEP,E") and has many desirable properties. In any embodiment, OBC has a melting point temperature $T_m$ within a range from 60, or 70, or 80 to 110, or 120° C. In any embodiment, the OBC has a crystallization temperature Tc within a range from 50, or 60 to 70, or 80° C. In any embodiment, the OBC has a number average molecular weight (Mn) within a range from 50, or 100 kg/mole to 200, or 300 kg/mole. In any embodiment, the OBC has a weight average molecular weight (Mw) within a range from 50, or 100 kg/mole to 200, or 300 kg/mole. In any embodiment, the OBC has a Mw/Mn value within a range from 0.9, or 1, or 1.1 to 1.2, or 1.3, or 1.4, or 1.5, or 1.8, or 2. In any embodiment, the OBC comprises lamella having a spacing within a range from 10, or 12 nm to 20, or 24, or 26, or 30 nm (SAXS/MAXS/WAXS at 20° C.).

Propylene-Based Elastomer

In any embodiment, the propylene-based elastomer is a random copolymer having crystalline regions interrupted by non-crystalline regions and within the range from 5 to 25 wt %, by weight of the propylene-based elastomer, of ethylene or C4 to C10 alpha-olefin derived units, and optionally diene-derived units, the remainder of the polymer being propylene-derived units. Not intended to be limited by any theory, it is believed that the non-crystalline regions may result from regions of non-crystallizable polypropylene segments and/or the inclusion of comonomer units. The crystallinity and the melting point of the propylene-based elastomer are reduced compared to highly isotactic polypropylene by the introduction of errors (stereo and region defects) in the insertion of propylene and/or by the presence of comonomer. The copolymer contains at least 60 wt % propylene-derived units by weight of the propylene-based elastomer. In any embodiment, the propylene-based elastomer is a propylene-based elastomer having limited crystallinity due to adjacent isotactic propylene units and a melting point as described herein. In other embodiments, the propylene-based elastomer is generally devoid of any substantial intermolecular heterogeneity in tacticity and comonomer composition, and also generally devoid of any substantial heterogeneity in intramolecular composition distribution.

The propylene-based elastomer contains greater than 50 wt %, preferably greater than 60 wt %, more preferably greater than 65 wt %, even more preferably greater than 75 wt % and up to 99 wt % propylene-derived units, based on the total weight of the propylene-based elastomer. In some preferable embodiments, the propylene-based elastomer includes propylene-derived units in an amount based on the weight of propylene-based elastomer of from 75 wt % to 95 wt %, more preferably 75 wt % to 92.5 wt %, and even more preferably 82.5 wt % to 92.5 wt %, and most preferably 82.5 wt % to 90 wt %. Correspondingly, the units, or comonomers, derived from at least one of ethylene or a C4 to C10 alpha-olefin may be present in an amount of 5, or 10, or 14 wt % to 22, or 25 wt % by weight of the elastomer.

The comonomer content may be adjusted so that the propylene-based elastomer having a heat of fusion of 100 J/g or less, or 75 J/g or less, a melting point ($T_m$) of 100° C. or 90° C. or less, and crystallinity of 2% to 65% of isotactic polypropylene, and preferably a melt flow rate ("MFR"), as measured at 230° C. and 2.16 kg weight, of less than 800 g/10 min.

The propylene-based elastomer may comprise more than one comonomer. Preferred embodiments of a propylene-based elastomer have more than one comonomer including propylene-ethylene-octene, propylene-ethylene-hexene, and propylene-ethylene-butene copolymers.

In embodiments where more than one comonomers derived from at least one of ethylene or a C4 to C10 alpha-olefin are present, the amount of each comonomer may be less than 5 wt % of the propylene-based elastomer, but the combined amount of comonomers by weight of the propylene-based elastomer is 5 wt % or greater.

In preferred embodiments, the comonomer is ethylene, 1-hexene, or 1-octene, and preferably in an amount of 5, or 10, or 14 wt % to 22, or 25 wt % based on the weight of the propylene-based elastomer.

In any embodiment, the propylene-based elastomer comprises ethylene-derived units. The propylene-based elastomer may comprise 5, or 10, or 14 wt % to 22, or 25 wt % of ethylene-derived units by weight of the propylene-based elastomer. In any embodiment, the propylene-based elastomer consists essentially of units derived from propylene and ethylene, i.e., the propylene-based elastomer does not contain any other comonomer in an amount typically present as impurities in the ethylene and/or propylene feedstreams used during polymerization or an amount that would materially affect the heat of fusion, melting point, crystallinity, or melt flow rate of the propylene-based elastomer, or any other comonomer intentionally added to the polymerization process.

In any embodiment, diene comonomer units are included in the propylene-based elastomer. Examples of the diene include, but not limited to, 5-ethylidene-2-norbornene, 5-vinyl-2-norbornene, divinylbenzene, 1,4-hexadiene, 5-methylene-2-norbornene, 1,6-octadiene, 5-methyl-1, 4-hexadiene, 3,7-dimethyl-1,6-octadiene, 1,3-cyclopentadiene, 1,4-cyclohexadiene, dicyclopentadiene, or a combination thereof. The amount of diene comonomer is equal to or more than 0 wt %, or 0.5 wt %, or 1 wt %, or 1.5 wt % and lower than, or equal to, 5 wt %, or 4 wt %, or 3 wt % or 2 wt % based on the weight of propylene-based elastomer.

The propylene-based elastomer has a heat of fusion ("Hf"), as determined by the Differential Scanning calorimetry ("DSC"), of 100 J/g or less, or 75 J/g or less, 70 J/g or less, 50 J/g or less, or 35 J/g or less. The propylene-based elastomer may have a lower limit $H_f$ of 0.5 J/g, 1 J/g, or 5 J/g. For example, the $H_f$ value may be anywhere from 1.0, 1.5, 3.0, 4.0, 6.0, or 7.0 J/g, to 30, 35, 40, 50, 60, 70, or 75 J/g.

The propylene-based elastomer may have a percent crystallinity, as determined according to the DSC procedure described herein, of 2% to 65%, preferably 0.5% to 40%, preferably 1% to 30%, and more preferably 5% to 35%, of isotactic polypropylene. The thermal energy for the highest order of propylene (i.e., 100% crystallinity) is estimated at 189 J/g. In any embodiment, the copolymer has a crystallinity in the range of 0.25% to 25%, or 0.5% to 22% of isotactic polypropylene.

In any embodiment, the propylene-derived units of the propylene-based elastomer have an isotactic triad fraction of 50% to 99%, more preferably 65% to 97% and more preferably 75% to 97%. In other embodiments, the first polymer has a triad tacticity as measured by $^{13}C$ NMR, of 75% or greater, 80% or greater, 82% or greater, 85% or greater, or 90% or greater. The triad tacticity of a polymer is the relative tacticity of a sequence of three adjacent propylene units, a chain consisting of head to tail bonds, expressed as a binary combination of m and r sequences. It is usually expressed as the ratio of the number of units of the specified tacticity to all of the propylene triads in the first polymer. The triad tacticity (mm fraction) of a propylene copolymer can be determined from a $^{13}C$ NMR spectrum of the propylene copolymer. The calculation of the triad tacticity is described in the U.S. Pat. No. 5,504,172, the entire contents of which are incorporated herein by reference.

The propylene-based elastomer may have a single peak melting transition as determined by DSC. In any embodiment, the copolymer has a primary peak transition of 90° C. or less, with a broad end-of-melt transition of 110° C. or greater. The peak "melting point" ("$T_m$") is defined as the temperature of the greatest heat absorption within the range of melting of the sample. However, the copolymer may show secondary melting peaks adjacent to the principal peak, and/or at the end-of-melt transition. For the purposes of this disclosure, such secondary melting peaks are considered together as a single melting point, with the highest of these peaks being considered the $T_m$ of the propylene-based elastomer. The propylene-based elastomer may have a $T_m$ of 100° C. or less, 90° C. or less, 80° C. or less, or 70° C. or less. In any embodiment, the propylene-based elastomer has a $T_m$ of 25° C. to 100° C., 25° C. to 85° C., 25° C. to 75° C., or 25° C. to 65° C. In any embodiment, the propylene-based elastomer has a $T_m$ of 30° C. to 80° C., preferably 30° C. to 70° C.

For the thermal properties of the propylene-based elastomers, Differential Scanning calorimetry ("DSC") was used. Such DSC data was obtained using a Perkin-Elmer DSC 7.5 mg to 10 mg of a sheet of the polymer to be tested was pressed at approximately 200° C. to 230° C., then removed with a punch die and annealed at room temperature for 48 hours. The samples were then sealed in aluminum sample pans. The DSC data was recorded by first cooling the sample to −50° C. and then gradually heating it to 200° C. at a rate of 10° C./minute. The sample was kept at 200° C. for 5 minutes before a second cooling-heating cycle was applied. Both the first and second cycle thermal events were recorded. Areas under the melting curves were measured and used to determine the heat of fusion and the degree of crystallinity. The percent crystallinity (X %) was calculated using the formula, X %=[area under the curve (Joules/gram)/B (Joules/gram)]*100, where B is the heat of fusion for the homopolymer of the major monomer component. These values for B were found from the Polymer Handbook, Fourth Edition, published by John Wiley and Sons, New York 1999. A value of 189 J/g (B) was used as the heat of fusion for 100% crystalline polypropylene. The melting temperature was measured and reported during the second heating cycle (or second melt).

In one or more embodiments, the propylene-based elastomer may have a Mooney viscosity [ML (1+4) @ 125° C.], as determined according to ASTM D-1646, of less than 100, in other embodiments less than 75, in other embodiments less than 60, and in other embodiments less than 30.

The propylene-based elastomer may have a density of 0.850 g/cm$^3$ to 0.920 g/cm$^3$, 0.860 g/cm$^3$ to 0.900 g/cm$^3$, preferably 0.860 g/cm$^3$ to 0.890 g/cm$^3$, at room temperature as measured per ASTM D-1505.

The first polymer preferably has a melt flow rate ("MFR") greater than 0.5 g/10 min, and less than or equal to 1,000 g/10 min, or less than or equal to 800 g/10 min, more preferably less than or equal to 500 g/10 min, more preferably less than or equal to 200 g/10 min, more preferably less than or equal to 100 g/10 min, more preferably less than or equal to 50 g/10 min. Particularly preferred embodiments include a propylene-based elastomer with an MFR of less than or equal to 25 g/10 min, such as from 1 to 25 g/10 min, more preferably 1 to 20 g/10 min. The MFR is determined according to ASTM D-1238, condition L (2.16 kg, 230° C.).

The propylene-based elastomer may have a weight average molecular weight ("Mw") of 5,000 to 5,000,000 g/mole, preferably 10,000 to 1,000,000 g/mole, and more preferably 50,000 to 400,000 g/mole; a number average molecular weight ("Mn") of 2,500 to 2,500,00 g/mole, preferably 10,000 to 250,000 g/mole, and more preferably 25,000 to 200,000 g/mole; and/or a z-average molecular weight ("Mz") of 10,000 to 7,000,000 g/mole, preferably 80,000 to 700,000 g/mole, and more preferably 100,000 to 500,000 g/mole. The propylene-based elastomer may have a molecular weight distribution (Mw/Mn, or "MWD") of 1.5 to 20, or 1.5 to 15, preferably 1.5 to 5, and more preferably 1.8 to 5, and most preferably 1.8 to 4.

The propylene-based elastomer may have an Elongation at Break of less than 2000%, less than 1000%, or less than 800%, as measured per ASTM D412.

Composition

Disclosed herein is a polymer composition comprising (or consisting essentially of, or consisting of) at least OBC; and at least one propylene-based elastomer, but most preferably only one propylene-based elastomer. In any embodiment the composition comprises within a range from 5, or 10, or 15 wt % to 30, or 40, or 50, or 60 wt % of the OBC, and within a range from 40, or 50, or 60, or 70 wt % to 85, or 90, or 95 wt % of the propylene-based elastomer. Most preferably the at least one OBC is poly(ethylene-b-ethylene/propylene-b-ethylene) comprising blocks comprising "ethylene" and blocks of "ethylene/propylene", which represents ethylene-propylene copolymer.

In any embodiment, the ethylene/propylene block of the poly(ethylene-b-ethylene/propylene-b-ethylene) has a propylene content within a range from 50, or 55, or 60 wt % to 65, or 70 wt % by weight of the ethylene/propylene block. Most preferably the ethylene/propylene block consists of ethylene-derived units and propylene-derived units.

In any embodiment, each ethylene block of the poly (ethylene-b-ethylene/propylene-b-ethylene) has a C3 to C8 content within a range from 2 wt % to 6, or 8, or 10, or 15 wt % by weight within each ethylene block; wherein the ethylene blocks consist of ethylene-derived units and C3 to C8-derived units, most preferably 1-butene-derived units.

The OBC preferably comprises two "ethylene" blocks for every one ethylene/propylene block. Most preferably the at least one OBC is the poly(ethylene-b-ethylene/propylene-b-ethylene) is derived from hydrogenated poly(1,4-butadiene-b-isoprene-b-1,4-butadiene).

In any embodiment, the compositions described herein are solution blends of the at least one OBC and the at least one propylene-based elastomer. This can be accomplished by combining the ingredients together in a solvent such as toluene or xylene at an elevated temperature until dissolved, then isolating the composition by evaporating the solvent. The compositions can also be formed by extrusion blending, or reactor blending wherein the ingredients in their respective solvents of polymerization are combined in series or parallel, followed by removal of the solvents.

In any embodiment, the OBC's described herein have a permanent set (7 day aging, 0 sec hold, 200% strain) within a range from 30, or 35, or 40 to 50, or 55% at 37° C., and within a range from 15, or 10 to 20, or 25% at 20° C.

In any embodiment, of the compositions described herein styrenic block copolymers are absent from the composition. By "styrenic block copolymers" what is meant are copolymer comprising at least one polymeric block having at least one styrene-derived unit. The styrenic block copolymers referred to can be of the "A-B" type, "B-A-B" type, or "A-B-A" type. Further, in any embodiment, the compositions described herein styrenic polymers are absent from the composition, where "styrenic polymers" are any polymers containing at least 1, or 2, or 5 wt % styrene-derived units. By "absent" what is meant is that none of the named materially is purposefully added to the composition at any stage of forming the composition, and if present, is below the limit of commercially occurring impurities in the components of the composition.

The compositions described herein have a number of uses. In any embodiment, the invention described herein includes fibers and fabrics comprising the composition. Further, in any embodiment, the composition is formed into, or made part of an elastic article. Some examples of elastic articles include diapers, surgical wear, hygiene wear, undergarments, and absorbent wear.

The various descriptive elements and numerical ranges disclosed herein for the inventive compositions can be combined with other descriptive elements and numerical ranges to describe the invention(s); further, for a given element, any upper numerical limit can be combined with any lower numerical limit described herein, including the examples in jurisdictions that allow such combinations. The features of the inventions are demonstrated in the following non-limiting examples.

EXAMPLES

DSC Measurements.

Differential Scanning calorimetry (DSC) was carried out on the OBC and blends using a TA Instrument Model Q-200. DSC measures the amount of energy absorbed or released by a sample when it is heated or cooled, providing quantitative and qualitative data on endothermic (heat absorption) and exothermic (heat evolution) processes. The sample was placed in a Zero Hermetic Pan and encapsulated with lid using a pan press. It sits upon a disc on a platform in the DSC cell. An empty reference pan sits on a symmetric platform in the DSC cell. Heat flow was measured by comparing the difference in temperature across the sample and the reference. Sample sizes are from 3.5 mg to 5 mg and were heated at rate of 10° C./min from −90° C. to 220° C. in nitrogen gas flowing at a rate of 50 ml/min. The samples were first heated from room temperature to 220° C. to remove any thermal history. Then they are cooled from 220° C. to −90° C., i.e. first cooling and heating back up from −90° C. to 220° C., i.e. second heating processes. All the DSC plots on first cooling and second heating were recorded. The melting point temperature, Tm, was recorded during the second heating and the crystallization temperature, Tc, was recorded during the first cooling.

GPC Measurements.

The column is calibrated with polystyrene and the mass is calibrated with NBS1475. For GPC measurements of olefin block copolymers, the molecular weight modeling is analyzed as a random EP copolymer with 35 wt % of ethylene from GPC-3D and GPC-4D, using a polystyrene standard; type of detectors: DRI (if 3D); Infrared (if 4D) (the trace shown in FIG. 1 is from GPC-4D); Temperature of elution: 145° C.; solvent of elution: TCB; rate of elution: 0.5 ml/min (if 3D); 1.0 ml/min (if 4D); type of columns: PLgel 10 μm Mix-B; MH constants (DRI): K=0.000579, α=0.695; and MH constants (IR): K=0.000175, α=0.670.

NMR Measurements.

500 MHz NMR instrument in TCE-d2 solvent at 75° C. and 4096 scans. NMR data of the EEPrE with and without dibutylhydroxytoluene (BHT) were collected after compression molding on the 2-day and 7-day aged samples. The samples are dissolved in TCE-d2 in 5 mm NMR tube at 135° C. until the sample is dissolved. There is no standard used. The TCE-d2 shows a peak at 5.98 ppm and used as the reference peak for our samples.

SAXS/MAXS/WAXS Measurements.

All small- and wide-angle X-ray scattering (SAXS/WAXS) were performed using an in-house SAXSLAB Ganesha 300XL+. The same sample preparation methods were used for X-ray measurements as for the elastic testing described below. Each sample was placed in a Linkam TST350 portable tensile stage, which was aligned to the X-ray beam. These samples provided good thermal contact and were controlled at 25° C.±0.1° C., and then at 37° C.±0.1° C. The incident wavelength was 0.154 nm from a CuK microfocus sealed tube source (Xenocs). All sample data were collected at sample-to-detector positions of 91 mm (WAXS) and 1041 mm (SAXS) and were held in a vacuum to minimize air scatter. The SAXS and WAXS were recorded using a Dectris Pilatus. Sample to detector distance was calibrated using a silver behenate standard. A 0-360° integration was performed on the 2D scattering patterns to yield a 1D I(q) versus q scattering profile. The WAXS patterns were then fitted to a combination of Lorentzian and Voigt functions to calculate the degree of crystallinity.

Elastic Property Measurements.

All the samples were compression molded at 170° C. followed by 2-day and 7-day aging at 25° C. The tensile testing was conducted on the Dynamic Mechanical Thermal Analysis (DMTA) instrument from TA Instrument ARES RSA G2 with dumbbell shape specimens measuring 3.5 mm (length)×2.5 mm (width)×0.25 mm (thickness). The specimens were pre-stretched at 0.1 N and underwent two stretch cycles up to 200% strain without sample removal from the grips at 0, 30 and 180 seconds holding (force relaxation) under 25° C. and 37° C. The pulling rate was 10 mm/min for tensile testing and 50 mm/min for strain to break. Due to the length constraint of the environmental chamber, the strain to break was only measured at 25° C. Three specimens were tested for each material under each condition, and the permanent set values recorded with an error of less than ±25%. The following parameters were measured and recorded at 25° C. and 37° C.:

Strain to break=% strain at which the specimen breaks at room temperature;
$1^{st}$ cycle permanent set (PS)=$1^{st}$ cycle unloading strain at zero load;
$2^{nd}$ cycle permanent set (PS)=$2^{nd}$ cycle unloading strain at zero load−$2^{nd}$ cycle loading strain at zero load;
Peak load=load at first cycle strain;
Hysteresis=area inside total first cycle curve;
$1^{st}$ cycle 30 s hold cycles=force relaxation=(peak load−peak unload)/(peak load)×100;
$1^{st}$ cycle 180 s hold cycles=force relaxation=(peak load−peak unload)/(peak load)×100.

Neat Olefin Block Copolymer.

The model olefin block copolymer (OBC) system was synthesized via living anionic polymerization of poly(1,4-butadiene-b-isoprene-b-1,4-butadiene) triblock copolymers followed by hydrogenation, resulting in a tri-block copolymer of poly(ethylene/butene-b-ethylene/propylene-b-ethylene/butene) (EEP$_r$E). The GPC data of the unhydrogenated first block, diblock and triblock are listed in Table 1. The $M_n$ values of each PE, EP$_r$ (random EP copolymer) and PE blocks are 23 k-129 k-18 k, respectively. Note that the PE blocks contain 6-8 wt % butene. Due to the nature of living anionic polymerization, there is always a certain amount of 1,2-butadiene insertion instead of 1,4-butadiene insertion, thus some butene-units remain after hydrogenation. If it were 100% 1,4-butadiene, then there would be 100% polyethylene blocks without any butene. In any case, the resultant unhydrogenated triblock molecular weight distribution is very narrow with an Mw/Mn of 1.03.

TABLE 1

GPC analysis the first, diblock and triblock before hydrogenation

| species | $M_n$, g/mol | $M_w$, g/mol | Mw/Mn |
|---|---|---|---|
| PBd first block | 23k | 29k | 1.26 |
| PBd-PI diblock | 152k | 164k | 1.08 |
| PBd-PI-PBd triblock | 170k | 175k | 1.03 |

Figure 2:
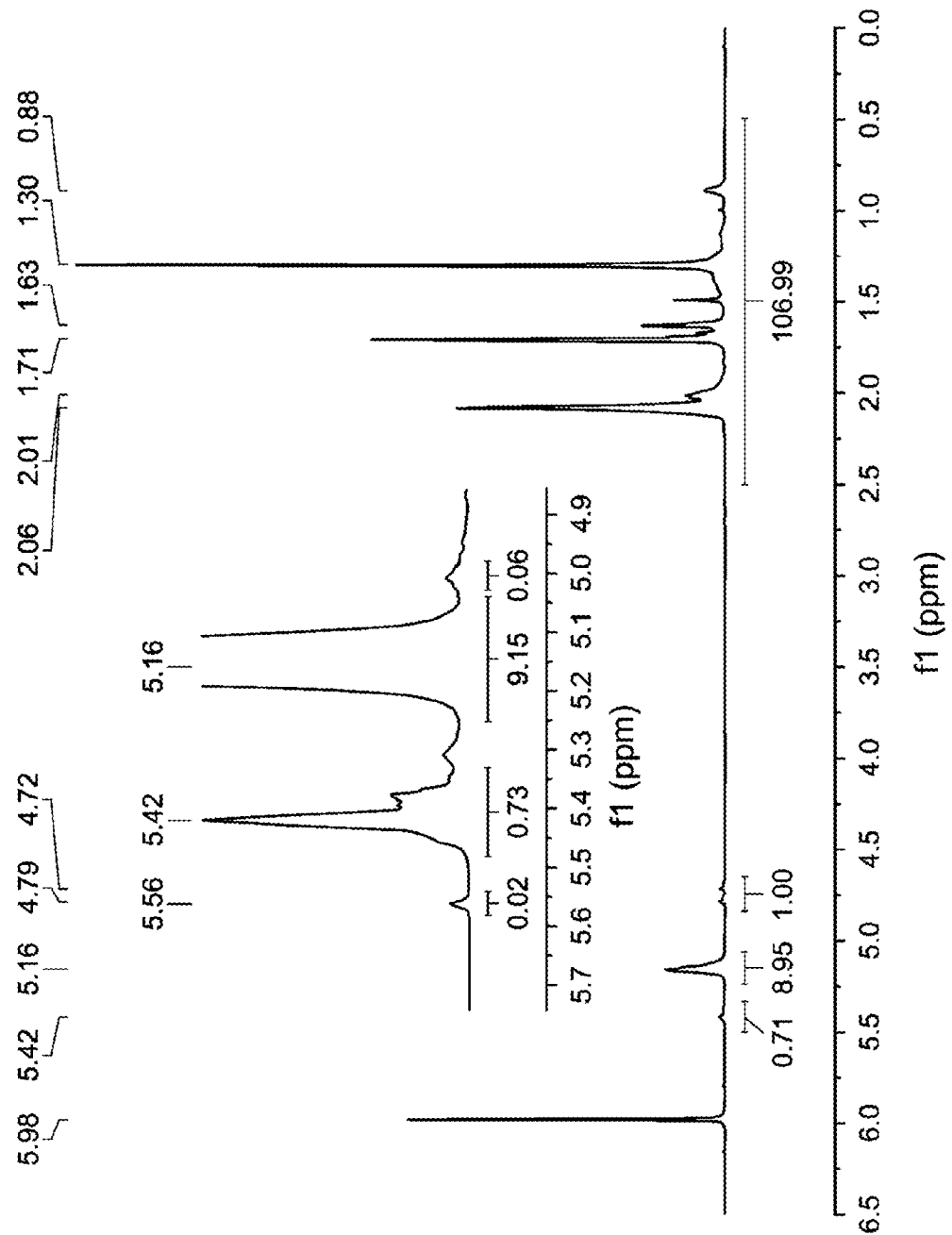
FIG. 2 is an NMR spectrum of the neat EEP$_r$E of the examples.

The GPC analysis of the hydrogenated product EEP$_r$E exhibits a unimodal molecular weight distribution as shown in FIG. 1. The NMR analysis was carried using a 500 MHz NMR instrument at 75° C. and 4096 scans to further characterize the EEP$_r$E. Using known resonance frequencies for the various protons, the EEP$_r$E was found to contain 1.5, 0.1 and 2.7 wt % unhydrogenated 1,4-butadiene and 1,2-isoprene, respectively. This is shown in FIG. 2.

Figure 3:
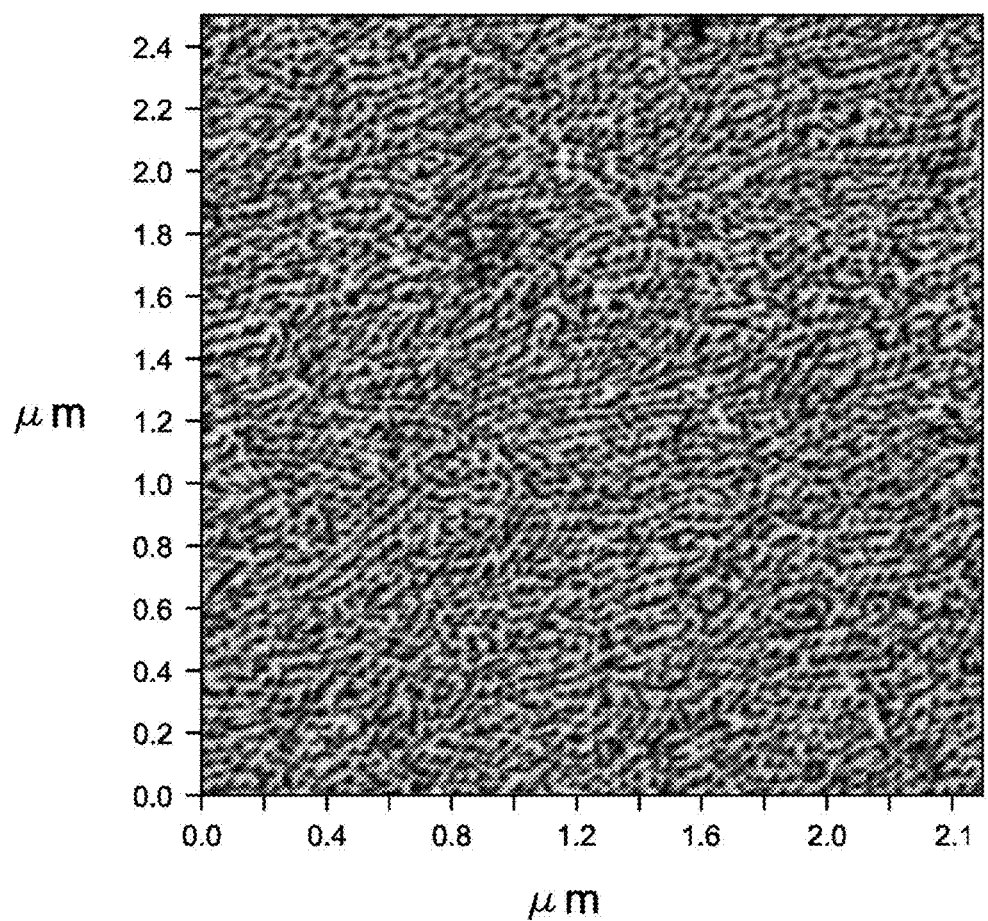
FIG. 3 is an AFM image (Phase 1) of the neat EEP$_r$E of the examples at 2.5 µm, darker regions are softer.

FIG. 3 shows an AFM image (Phase 1) of EEP$_r$E at 2.5 μm. Some hexagonal spheres were noted, but not rods. Some parts appear to be bi-continuous structures. The AFM did not resolve the lamellae within the hard (PE) domains as the contrast between the soft (PEP) domains and the overall PE domains is much higher than between amorphous and lamellar within the PE domains.

Figure 4:
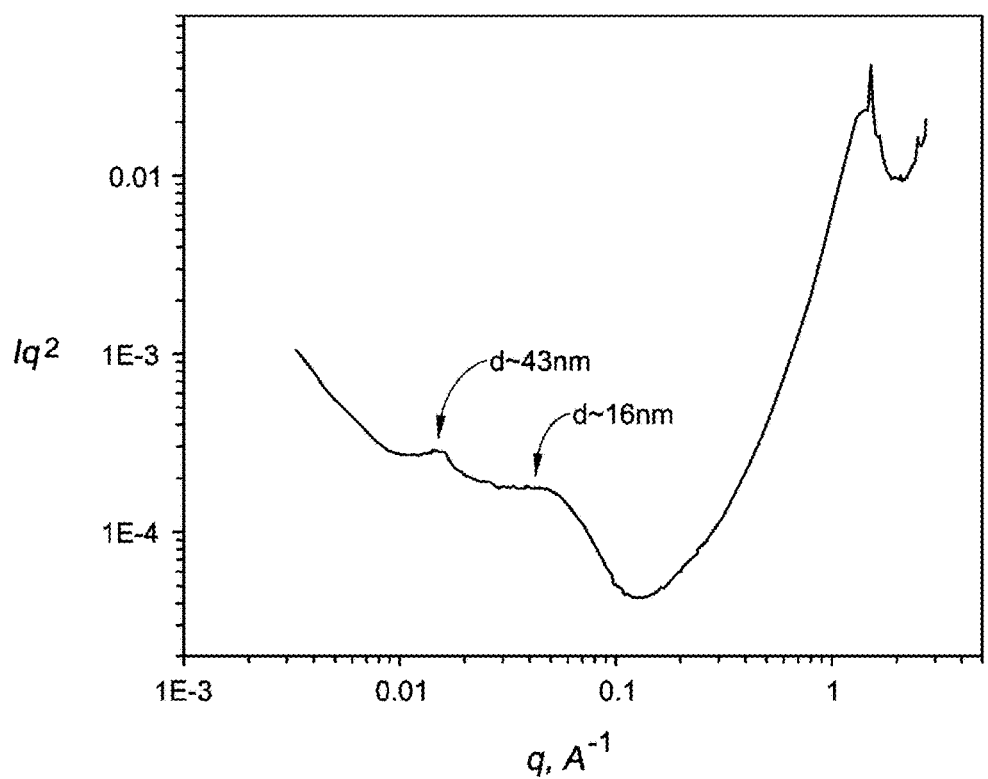
FIG. 4 is a SAXS/MAXS/WAXS spectra at 25° C. of the neat EEP$_r$E of the examples.

FIG. 4 shows the SAXS/MAXS/WAXS data obtained for the exemplary inventive EEP$_r$E. The peak corresponding to the block segregation (d of 43 nm) is faint because the long distance peak (d of 16 nm) is also present. The BCP peak is consistent with the distance observed in AFM.

Tensile testing was carried out with dumbbell shape geometry from the DMTA instrument in L1207, after 2-day and 7-day aging at 25° C. The specimen size was 3.50 mm×0.25 mm and the pulling speed was 10 mm/min. 200% cycle strain was applied across all materials with 2 stretch cycles performed without sample removal from grips. A 0.1 N pre-stretch was used to prevent samples from slagging. No hold, 30 and 180 second hold (force relaxation) at 200% strain. Three specimens are run under each testing condition. The $1^{st}$ cycle permanent set (PS) was the $1^{st}$ cycle unloading strain at zero load and the $2^{nd}$ cycle permanent set is the $2^{nd}$ cycle unloading strain at zero load minus the $2^{nd}$ cycle loading strain at zero load.

Table 2 shows the hysteresis plots and the numerical hysteresis values at 200% strain on EEP$_r$E, Kraton™ ("KG") 1567, and Vistamaxx™ propylene-based elastomers ("VM") at body and room temperatures (37° C. and 25° C., respectively). The EEP$_r$E approximates Kraton polymers in terms of the peak load and the permanent set, but does have larger mechanical hysteresis. At 37° C., Vistamaxx propylene-based elastomer has softer stretch and larger permanent set and hysteresis.

TABLE 2

Hysteresis values in percentage for EEPrE, Kraton and Vistamaxx propylene-based elastomer at 37° C. and 20° C. temperature, respectively

| species | 1$^{st}$ cycle (%) | 2$^{nd}$ cycle (%) |
|---|---|---|
| 25° C. | | |
| EEP$_r$E | 36.28 | 19.33 |
| KG1657 | 19.70 | 10.42 |
| VM6102 | 51.57 | 31.52 |
| 37° C. | | |
| EEP$_r$E | 41.32 | 22.17 |
| KG1657 | 23.94 | 14.38 |
| VM6102 | 65.91 | 32.48 |

Table 3 lists the NMR, density, MI, GPC and DSC results on the EEP$_r$E, commercial Kraton, poly(styrene-b-ethylene/butene-b-styrene) ("SEBS") purchased from Sigma-Aldrich, Vistamaxx 6102, and Vistamaxx 7010, propylene-based elastomers, and commercial Dow Infuse™ ethylene-octene block copolymers (OBC-1 and OBC-2, corresponding to D9107 and D9507, respectively). Tables 4A and 4B show the first permanent set of the model system and some benchmark materials at room and body temperatures (25° C. and 37° C., respectively) after 200% strain at 0, 30 seconds and 180 seconds holding. The elastic performance depends on the holding time and the temperature. In general, the permanent set values increases with temperature and prolonged holding. The model OBC system EEP$_r$E approximates Kraton polymer at 25° C. and 37° C. and it maintains a permanent set at 37° C. In addition, EEP$_r$E has the smallest change in permanent set values from 25° C. to 37° C.

TABLE 3

NMR, density, MI, GPC and DSC results on the EEP$_r$E and several benchmark materials

| Materials | Minority monomer derived units, wt % | Density (g/cm$^3$) | MI @190° C. & 2.16 kg (g/10 min) | Mn, GPC (g/mol) | Mw, GPC (g/mol) | Mw/Mn, GPC | T$_m$, DSC (° C.) | T$_c$, DSC (° C.) |
|---|---|---|---|---|---|---|---|---|
| EEP$_r$E | C3 = 27 | — | — | 102 k | 134 k | 1.31 | 98.19 | 66.30 |
| KG1657 | Styrene = 13 | 0.9 | 22 | — | — | — | — | — |
| SEBS | Styrene = 29 | — | — | — | — | — | — | — |
| VM6102 | C2 = 16 | 0.862 | 1.4 | 112 k | 231 k | 2.00 | 109.35 | 22.24 |
| VM7010 | C2 = 17 | 0.861 | 1.3 | 73 k | 222 k | 3.02 | 108.44 | 20.61 |
| OBC-1 | C8 = 28 | 0.866 | 1.0 | 82 k | 174 k | 2.12 | 122.91 | 85.28 |
| OBC-2 | C8 = 43 | 0.866 | 5.0 | 58 k | 117 k | 2.01 | 122.91 | 93.82 |

TABLE 4A

Permanent Set for Model and Benchmark Systems

| Time holding (sec) | EEP$_r$E | | KG1657 | | SEBS | |
|---|---|---|---|---|---|---|
| | 25° C. | 37° C. | 25° C. | 37° C. | 25° C. | 37° C. |
| 0 | 16 | 22 | 15 | 18 | 17 | 16 |
| 30 | 20 | 22 | 27 | 22 | 19 | 18 |
| 180 | 25 | 27 | 22 | 32 | 20 | 21 |

TABLE 4B

Permanent Set for Model and Benchmark Systems

| Time holding (sec) | VM6102 | | VM7010 | | OBC-1 | | OBC-2 | |
|---|---|---|---|---|---|---|---|---|
| | 25° C. | 37° C. | 25° C. | 37° C. | 25° C. | 37° C. | 25° C. | 37° C. |
| 0 | 28 | 41 | 23 | 42 | 28 | 35 | 45 | 72 |
| 30 | 27 | 51 | 26 | 46 | 31 | 41 | 51 | 89 |
| 180 | 30 | 64 | 29 | 62 | 39 | 51 | 60 | 102 |

Figure 5:
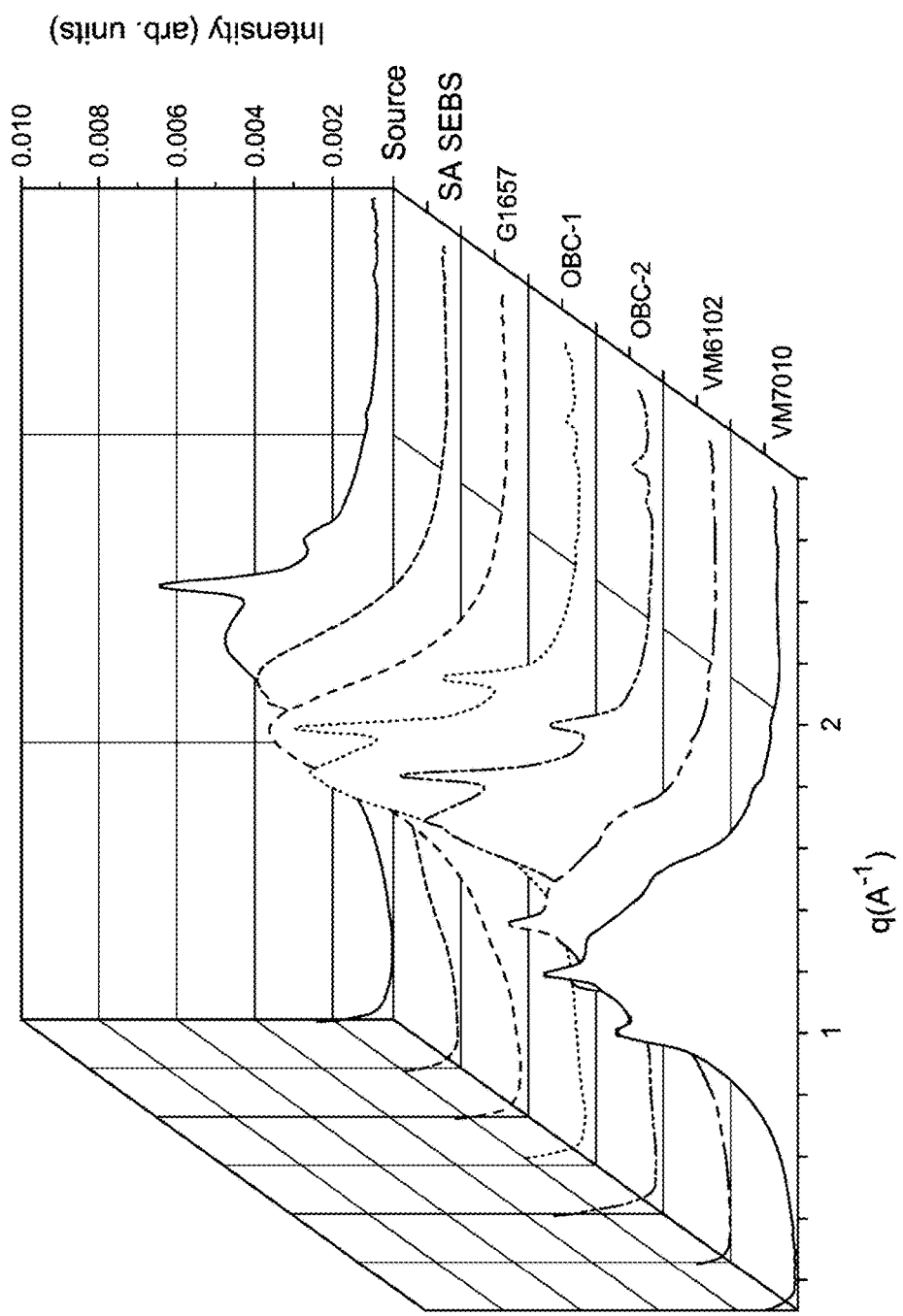
FIG. 5 are WAXS traces at 25° C. after 2 days of aging of the neat EEP$_r$E of the examples and other benchmark polymers as labeled.
Figure 6:
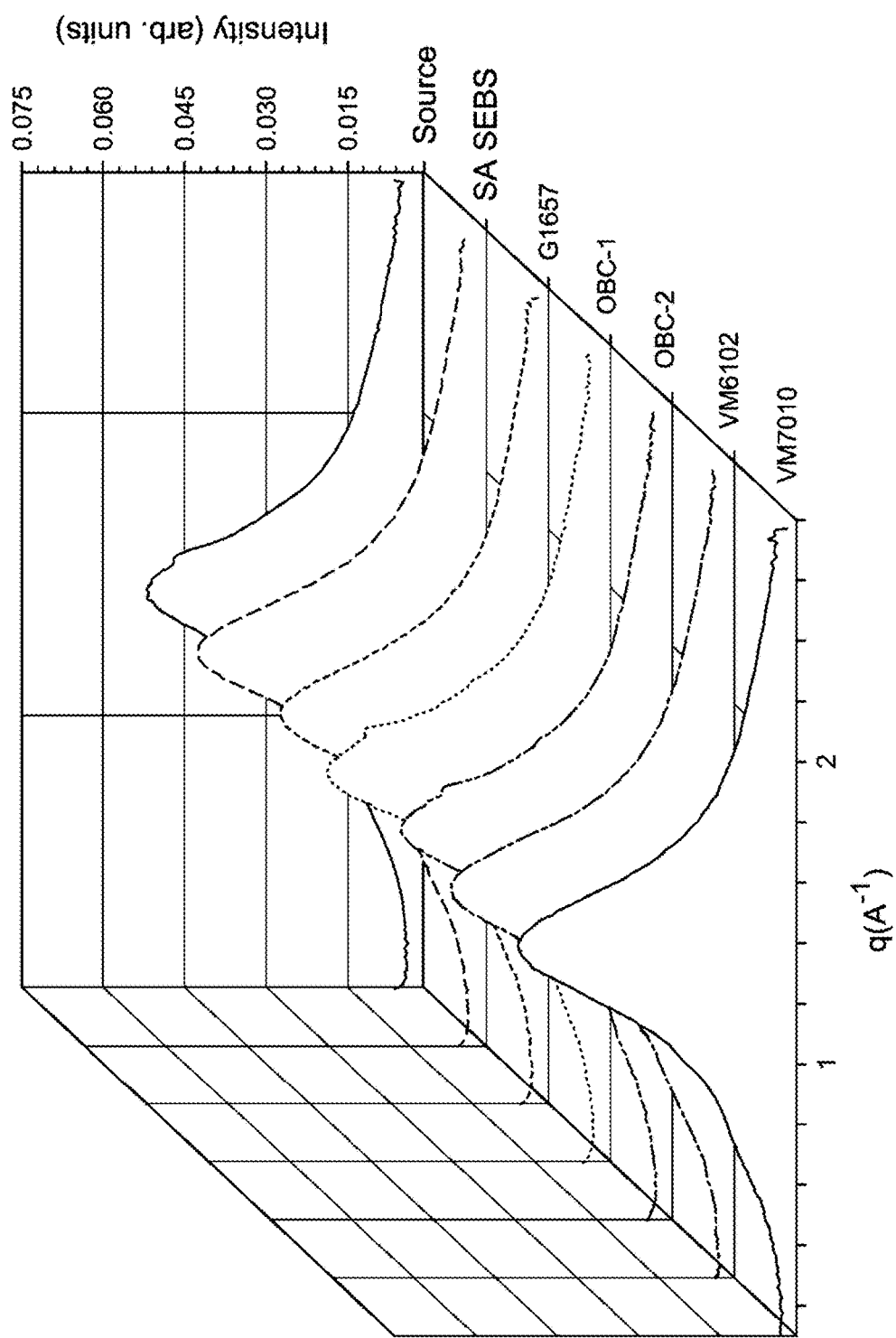
FIG. 6 are WAXS traces at 37° C. after 2 days of aging of the neat EEP$_r$E of the examples and other benchmark polymers as labeled.

FIG. 5 and FIG. 6 show the WAXS data of EEP$_r$E, Kraton, Vistamaxx propylene-based elastomer and commercial OBC polymers after 2-days of aging at 20° C. and 37° C. respectively. Similar crystallinity behavior is observed for each category of the materials. Kraton polymers do not have crystalline peaks due to the lack of crystalline blocks. The crystallinity percentage decreases dramatically with temperature for olefinic polymers. At 20° C., there are orthorhombic peaks for PE in EEP$_r$E and overall crystallinity is 5.6%. Alpha crystals of PP are present for Vistamaxx propylene-based elastomer yet due to the breadth of these peaks, we can say that these crystals are very small and possess many defects. Due to no SAXS signal, it appears that the Vistamaxx crystals do not stack into a regular ordered array. Commercial OBC polymers display ethylene crystallinity at levels of 6-7%. In addition these polymers also exhibit a monoclinic crystalline phase, typically observed for crystals with a high defect density. At 37° C., little crystallinity (<1%) was left for EEP$_r$E and commercial OBC polymers. For Vistamaxx propylene-based elastomer materials, the crystallinity appears to completely go away based on the data. The crystallinity percentage relates to the elastomeric properties for olefinic polymers.

Blends of Olefin Block Copolymer and Propylene-Based Elastomer.

Examples of inventive compositions had targeted concentrations of 10, 25 and 50 wt % of EEP$_r$E in VM 6102. For each solution blending experiment, the following procedure was carried out in order: All solid ingredients were added to a round bottom flask with a magnetic stir bar, including about 0.2 to 1 grams of EEP$_r$E, then xylenes (80-100 mL) were added to the solids, followed by heated stirring, setting the temperature of the heating block at 110° C. The mixture was then stirred at 110° C. for 3 hr to form a homogeneous solution. The homogeneous mixture was then poured into a clean flask and cooled overnight to afford a thin film. To that container was added another 100 mL of xylenes which was heated at 110° C. for 10 min while stirring to form a homogeneous solution which was then poured into another clean flask. Finally, the solvent was evaporated, resulting in a solid material that was further dried at 50° C. in a vacuum oven for 24 hr, affording the final solid composition.

Table 5 lists the composition of three solution blends of EEP$_r$E model OBC and Vistamaxx 6102 propylene-based elastomer in xylene. The target OBC wt % is 10, 25 and 50 wt %, respectively. Each contains 0.2 wt % of Irganox™ 1010.

TABLE 5

Composition of solution blends of EEP$_r$E and Vistamaxx ™ 6102 polymers

| Sample Blend | EEP$_r$E, g | VM ™ 6102, g | Irganox 1010, g | Wt. % of EEP$_r$E |
|---|---|---|---|---|
| EEP$_r$E$_{10}$-VM$_{90}$ | 0.207 | 1.816 | 0.0047 | 10.2 |
| EEP$_r$E$_{25}$-VM$_{75}$ | 0.505 | 1.510 | 0.0040 | 25.0 |
| EEP$_r$E$_{50}$-VM$_{50}$ | 1.004 | 1.016 | 0.0049 | 49.6 |

Tables 6A and 6B show the first permanent set values of the neat materials and, the three solution blends and two commercial OBCs after 7-day aging at 20° C. The tensile testing was conducted at 20° C. and 37° C. with 0, 30 and 180 seconds holding. The blend with 10 wt % of OBC does not perform as well as the neat Vistamaxx 6102 propylene-based elastomer. With higher OBC content of 25 wt % and 50 wt %, the blends show smaller permanent set values than the neat Vistamaxx 6102 propylene-based elastomer in general. At 25 wt % OBC, the blends approximates the 37° C. performance of EEPrE.

TABLE 6A

Permanent Set at 200% Strain for Vistamaxx 6102 and Blends 7-day aging

| Time holding (sec) | VM 6102 | | EEP$_r$E 10 wt % | | EEP$_r$E 25 wt % | |
|---|---|---|---|---|---|---|
| | 25° C. | 37° C. | 25° C. | 37° C. | 25° C. | 37° C. |
| 0 | 28 | 41 | 27 | 50 | 21 | 36 |
| 30 | 27 | 51 | 30 | 55 | 26 | 43 |
| 180 | 30 | 64 | 35 | 71 | 30 | 54 |

TABLE 6B

Permanent Set at 200% Strain for Blends and EEPrE 7-day aging

| Time holding (sec) | EEP$_r$E 50 wt % | | EEPrE | |
|---|---|---|---|---|
| | 25° C. | 37° C. | 25° C. | 37° C. |
| 0 | 28 | 45 | 17 | 22 |
| 30 | 32 | 48 | 20 | 22 |
| 180 | 37 | 59 | 25 | 27 |

When numerical lower limits and numerical upper limits are listed herein, ranges from any lower limit to any upper limit are contemplated. The term "comprising" is synonymous with the term "including". Likewise whenever a composition, an element or a group of components is preceded with the transitional phrase "comprising", it is understood that we also contemplate the same composition or group of components with transitional phrases "consisting essentially of", "consisting of", "selected from the group of consisting of", or "is" preceding the recitation of the composition, component, or components, and vice versa.

As used herein, "consisting essentially of" means that the claimed composition includes only the named components and no additional components that will alter its measured properties by any more than 20%, and most preferably means that additional components are present to a level of less than 5, or 4, or 3, or 2 wt % by weight of the composition. Such additional components can include, for example, fillers, colorants, antioxidants, anti-UV additives, curatives and cross-linking agents, aliphatic and/or cyclic containing oligomers or polymers, often referred to as hydrocarbon resins, and other additives well known in the art.

For all jurisdictions in which the doctrine of "incorporation by reference" applies, all of the test methods, patent publications, patents and reference articles are hereby incorporated by reference either in their entirety or for the relevant portion for which they are referenced.

The invention claimed is:
1. A polymer composition comprising:
within a range from 5 wt % to 60 wt % of at least one olefin block copolymer having an Mw/Mn within a range from 1 to 2; and
within a range from 40 wt % to 95 wt % of at least one propylene-based elastomer having a T$_m$ of 100° C. or less,
wherein the polymer composition has a permanent set (7 day aging, 0 sec hold, 200% strain) within a range from 30 to 55% at 37° C., and within a range from 10 to 25% at 20° C., when measured on a dumbbell shape specimen measuring 3.5 mm in length by 2.5 mm in width by 0.25 mm in thickness.

2. A polymer composition comprising:
   a) from 5 wt % to 60 wt % of poly(ethylene-b-ethylene/propylene-b-ethylene) olefin block copolymer, said copolymer having an Mw/Mn within a range from 1 to 2; and
   b) from 40 wt % to 95 wt % of at least one propylene-based elastomer having a $T_m$ of 100° C. or less.

3. The composition of claim 2, wherein the poly(ethylene-b-ethylene/propylene-b-ethylene) is derived from hydrogenated poly(1,4-butadiene-b-isoprene-b-1,4-butadiene).

4. The composition of claim 2, wherein the ethylene/propylene block of the poly(ethylene-b-ethylene/propylene-b-ethylene) has a propylene content within a range from 50 wt % to 70 wt % by weight of the ethylene/propylene block; wherein the ethylene/propylene block consists of ethylene-derived units and propylene-derived units.

5. The composition of claim 2, wherein each ethylene block of the poly(ethylene-b-ethylene/propylene-b-ethylene) has an C3 to C8 content within a range from 2 wt % to 15 wt % by weight within each ethylene block; wherein the ethylene blocks consist of ethylene-derived units and C3 to C8-derived units.

6. The composition of claim 1, wherein the propylene-based elastomer comprises within a range from 10 wt % to 22 wt % ethylene or C4 to C12 α-olefin derived units.

7. The composition of claim 1, wherein the propylene-based elastomer has a heat of fusion of less than 100 J/g.

8. The composition of claim 1, wherein the olefin block copolymer has a melting point temperature $T_m$ within a range from 60 to 120° C.

9. The composition of claim 1, wherein the olefin block copolymer has a crystallization temperature Tc within a range from 50 to 80° C.

10. The composition of claim 1, wherein the olefin block copolymer has a number average molecular weight (Mn) within a range from 50 kg/mole to 300 kg/mole.

11. The composition of claim 1, wherein the olefin block copolymer has a weight average molecular weight (Mw) within a range from 50 kg/mole to 300 kg/mole.

12. The composition of claim 1, wherein the olefin block copolymer has an Mw/Mn value within a range from 1 to 1.5.

13. The composition of claim 1, wherein the olefin block copolymer comprises lamella having a spacing within a range from 10 nm to 30 nm (small, medium, wide angle X-ray scattering at 20° C.).

14. The composition of claim 1, wherein the composition is solution blend of the olefin block copolymer and propylene-based elastomer.

15. The composition of claim 1, having a permanent set (7 day aging, 0 sec hold, 200% strain) within a range from 35 to 55% at 37° C., and within a range from 15 to 25% at 20° C., when measured on a dumbbell shape specimen measuring 3.5 mm in length by 2.5 mm in width by 0.25 mm in thickness.

16. The composition of claim 1, wherein styrenic block copolymers are absent from the composition.

17. A fiber comprising the composition of claim 1.

18. An elastic article comprising the composition of claim 1.

19. The elastic article of claim 18, comprising diapers, surgical wear, hygiene wear, undergarments, and absorbent wear.

20. The composition of claim 1, wherein the olefin block copolymer has an Mw/Mn value within a range from 1.1 to 2.

21. The composition of claim 2, wherein each ethylene block of the poly(ethylene-b-ethylene/propylene-b-ethylene) has an C3 to C8 content within a range from 2 wt % to 15 wt % by weight within each ethylene block; wherein the ethylene blocks consist of ethylene-derived units and 1-butene-derived units.

22. A Fabric comprising the composition of claim 1.

23. The composition of claim 1 wherein the olefin block copolymer has a melting point temperature $T_m$ within a range from 70 to 120° C.

24. The composition of claim 2, wherein the propylene-based elastomer comprises within a range from 10 wt % to 22 wt % ethylene or C4 to C12 α-olefin derived units.

25. The composition of claim 2, wherein the propylene-based elastomer has a heat of fusion of less than 100 J/g.

26. The composition of claim 2, wherein the olefin block copolymer has a melting point temperature $T_m$ within a range from 60 to 120° C.

27. The composition of claim 2, wherein the olefin block copolymer has a crystallization temperature Tc within a range from 50 to 80° C.

28. The composition of claim 2, wherein the olefin block copolymer has a number average molecular weight (Mn) within a range from 50 kg/mole to 300 kg/mole.

29. The composition of claim 2, wherein the olefin block copolymer has a weight average molecular weight (Mw) within a range from 50 kg/mole to 300 kg/mole.

30. The composition of claim 2, wherein the olefin block copolymer has an Mw/Mn value within a range from 1 to 1.5.

31. The composition of claim 2, wherein the olefin block copolymer comprises lamella having a spacing within a range from 10 nm to 30 nm (small, medium, wide angle X-ray scattering at 20° C.).

32. The composition of claim 2, wherein the composition is solution blend of the olefin block copolymer and propylene-based elastomer.

33. The composition of claim 2, having a permanent set (7 day aging, 0 sec hold, 200% strain) within a range from 35 to 55% at 37° C., and within a range from 15 to 25% at 20° C., when measured on a dumbbell shape specimen measuring 3.5 mm in length by 2.5 mm in width by 0.25 mm in thickness.

34. The composition of claim 2, wherein styrenic block copolymers are absent from the composition.

35. A polymer composition comprising:
   a) from 5 wt % to 60 wt % of poly(ethylene/butene-b-ethylene/propylene-b-ethylene/butene) olefin block copolymer, said copolymer having an Mw/Mn within a range from 1 to 2; and
   b) from 40 wt % to 95 wt % of at least one propylene-based elastomer having a $T_m$ of 100° C. or less.

36. The composition of claim 35, wherein the ethylene/propylene block of the poly(ethylene/butene-b-ethylene/propylene-b-ethylene/butene) has a propylene content within a range from 50 wt % to 70 wt % by weight of the ethylene/propylene block; wherein the ethylene/propylene block consists of ethylene-derived units and propylene-derived units.

37. The composition of claim 35, wherein each ethylene block of the poly(ethylene/butene-b-ethylene/propylene-b-ethylene/butene) has an C3 to C8 content within a range from 2 wt % to 15 wt % by weight within each ethylene block; wherein the ethylene blocks consist of ethylene-derived units and C3 to C8-derived units.

38. The composition of claim 36, wherein each ethylene block of the poly(ethylene/butene-b-ethylene/propylene-b-ethylene/butene) has an C3 to C8 content within a range from 2 wt % to 15 wt % by weight within each ethylene block; wherein the ethylene blocks consist of ethylene-derived units and 1-butene-derived units.

* * * * *